US010548901B2

(12) United States Patent
Lang et al.

(10) Patent No.: US 10,548,901 B2
(45) Date of Patent: Feb. 4, 2020

(54) MELOXICAM FOR THE TREATMENT OF RESPIRATORY DISEASES IN PIGS

(71) Applicant: Boehringer Ingelheim Vetmedica GmbH, Ingelheim am Rhein (DE)

(72) Inventors: Ingo Lang, Ingelheim am Rhein (DE); Ioannis Papatsas, Salonika (GR)

(*) Notice: Subject to any disclaimer, the term of this patent is extended or adjusted under 35 U.S.C. 154(b) by 0 days.

(21) Appl. No.: 15/908,470

(22) Filed: Feb. 28, 2018

(65) Prior Publication Data
US 2018/0185380 A1 Jul. 5, 2018

Related U.S. Application Data

(60) Continuation of application No. 14/183,744, filed on Feb. 19, 2014, now abandoned, which is a division of application No. 12/114,509, filed on May 2, 2008, now abandoned, which is a continuation of application No. 11/047,920, filed on Feb. 1, 2005, now abandoned.

(30) Foreign Application Priority Data

Feb. 23, 2004 (EP) .................................. 04004054

(51) Int. Cl.
*A61K 31/5415* (2006.01)
*A61K 45/06* (2006.01)
*A61K 31/65* (2006.01)

(52) U.S. Cl.
CPC .......... *A61K 31/5415* (2013.01); *A61K 31/65* (2013.01); *A61K 45/06* (2013.01)

(58) Field of Classification Search
CPC ..... A61K 31/5415; A61K 31/65; A61K 45/06
See application file for complete search history.

(56) References Cited

U.S. PATENT DOCUMENTS

| | | | |
|---|---|---|---|
| 2,795,529 A | 6/1957 | Alburn et al. | |
| 3,089,818 A | 5/1963 | Stone et al. | |
| 3,288,675 A | 11/1966 | Newmark et al. | |
| 3,849,549 A | 11/1974 | Dempski et al. | |
| 3,931,212 A | 1/1976 | Satzinger et al. | |
| 3,947,576 A | 3/1976 | Kuczkowski et al. | |
| 4,233,299 A | 11/1980 | Trummlitz et al. | |
| 4,446,144 A | 5/1984 | von Daehne | |
| 4,447,443 A | 5/1984 | Goldenberg | |
| 4,482,554 A | 11/1984 | Gebhardt et al. | |
| 4,543,200 A | 9/1985 | Sherman | |
| 4,628,053 A | 12/1986 | Fries | |
| 4,687,662 A | 8/1987 | Schobel | |
| 4,702,919 A | 10/1987 | Kitamori et al. | |
| 4,748,174 A | 5/1988 | Veronesi | |
| 4,794,117 A | 12/1988 | Corbiere | |
| 4,802,926 A | 2/1989 | Kussendrager et al. | |
| 4,835,187 A | 5/1989 | Reuter et al. | |
| 4,942,167 A | 7/1990 | Chiesi et al. | |
| 5,026,560 A | 6/1991 | Makino et al. | |
| 5,085,868 A | 2/1992 | Mattsson et al. | |
| 5,169,847 A | 12/1992 | Nagy et al. | |
| 5,178,878 A | 1/1993 | Wehling et al. | |
| 5,283,065 A | 2/1994 | Doyon et al. | |
| 5,304,561 A | 4/1994 | Sarfarazi | |
| 5,360,611 A | 11/1994 | Robertson et al. | |
| 5,380,934 A | 1/1995 | Inoue et al. | |
| 5,414,011 A | 5/1995 | Fu et al. | |
| 5,460,828 A | 10/1995 | Santus et al. | |
| 5,464,632 A | 11/1995 | Cousin et al. | |
| 5,489,439 A | 2/1996 | Bola | |
| 5,552,160 A | 9/1996 | Liversidge et al. | |
| 5,556,639 A | 9/1996 | Fielden | |
| 5,599,535 A | 2/1997 | Polansky et al. | |
| 5,654,003 A | 8/1997 | Fuisz et al. | |
| 5,674,888 A | 10/1997 | Polansky et al. | |
| 5,700,816 A * | 12/1997 | Isakson .................. | A61K 45/06 514/317 |
| 5,792,838 A | 8/1998 | Smith et al. | |
| 5,811,446 A | 9/1998 | Thomas | |
| 5,824,658 A | 10/1998 | Falk et al. | |
| 5,886,030 A | 3/1999 | Maniar | |
| 5,891,129 A | 4/1999 | Daubert et al. | |
| 5,962,012 A | 10/1999 | Lin et al. | |
| 6,046,191 A | 4/2000 | Hamley et al. | |
| 6,048,557 A | 4/2000 | Van Den Burg et al. | |
| 6,053,890 A | 4/2000 | Moreau Defarges et al. | |
| 6,063,783 A | 5/2000 | Pineiro et al. | |
| 6,071,539 A | 6/2000 | Robinson et al. | |
| 6,077,864 A | 6/2000 | Burgess et al. | |

(Continued)

FOREIGN PATENT DOCUMENTS

AU 673675 B2 11/1996
AU 762464 B2 6/2003

(Continued)

OTHER PUBLICATIONS

Straus et al., "New Evidence for Stroke Prevention: Clinical Applications". The Journal of the American Medical Association, vol. 288, No. 11, Sep. 2002, pp. 1396-1398.
Straus et al., "New Evidence for Stroke Prevention: Scientific Review". The Journal of the American Medical Association, vol. 288, No. 11, Sep. 2002, pp. 1388-1395.
Sunose et al., "The Effect of Cyclooxygenase 2 Inhibitor, FK3311, on Ischemia-Reperfusion Injury in Canine Lung Transplantation". Journal of Heart and Lung Transplantation, vol. 19, No. 1, Jan. 2000, p. 40.
Swamy et al., "Orodispersible tablets of meloxicam using disintegrant blends for improved efficacy"., Indian Journal of Pharmaceutical Science, vol. 69, No. 6, 2007, pp. 836-840. [Accessed at http://ijpsonline.com/article.asp?issn=0250-474X;year=2007;volume=69;issue=6;spa . . . on Jun. 16, 2013].

(Continued)

*Primary Examiner* — Snigdha Maewall
(74) *Attorney, Agent, or Firm* — Judy Jarecki-Black

(57) ABSTRACT

A method of treating or preventing a respiratory disease in a pig is described that includes administering to the pig in need thereof an effective amount of meloxicam or a pharmaceutically acceptable salt thereof.

9 Claims, 2 Drawing Sheets

(56) References Cited

U.S. PATENT DOCUMENTS

| | | | |
|---|---|---|---|
| 6,090,800 A | 7/2000 | Unger et al. | |
| 6,106,862 A | 8/2000 | Chen et al. | |
| 6,136,804 A | 10/2000 | Nichtberger | |
| 6,156,349 A | 12/2000 | Steinbach et al. | |
| 6,166,012 A | 12/2000 | Muller et al. | |
| 6,180,136 B1 * | 1/2001 | Larson | A61K 9/0019 264/4.1 |
| 6,183,779 B1 | 2/2001 | Ouali et al. | |
| 6,184,220 B1 | 2/2001 | Turck et al. | |
| 6,187,800 B1 | 2/2001 | Suri et al. | |
| 6,221,377 B1 | 4/2001 | Meyer | |
| 6,284,269 B1 | 9/2001 | Struengmann et al. | |
| 6,319,519 B2 | 11/2001 | Woolfe et al. | |
| 6,495,603 B1 | 12/2002 | Miyake et al. | |
| 6,550,955 B2 | 4/2003 | D'Silva | |
| 6,599,529 B1 | 7/2003 | Skinhøj et al. | |
| 6,605,295 B1 | 8/2003 | Bellmann et al. | |
| 6,630,056 B1 | 10/2003 | Thibierge et al. | |
| 6,669,957 B1 | 12/2003 | Laruelle et al. | |
| 6,682,747 B1 | 1/2004 | Turck et al. | |
| 6,869,948 B1 | 3/2005 | Bock et al. | |
| 6,986,346 B2 | 1/2006 | Hochrainer et al. | |
| 7,105,512 B2 | 9/2006 | Morizono et al. | |
| 7,969,206 B2 | 6/2011 | Ito | |
| 8,337,892 B1 | 12/2012 | Couaraze et al. | |
| 8,920,820 B2 | 12/2014 | Folger et al. | |
| 2001/0055569 A1 | 12/2001 | Davis et al. | |
| 2002/0006440 A1 | 1/2002 | Cherukuri | |
| 2002/0016342 A1 | 2/2002 | Scolnick et al. | |
| 2002/0035107 A1 | 3/2002 | Henke et al. | |
| 2002/0058908 A1 | 5/2002 | Zierenberg et al. | |
| 2002/0068088 A1 | 6/2002 | Gruber | |
| 2002/0077328 A1 | 6/2002 | Hassan et al. | |
| 2002/0099049 A1 | 7/2002 | Burch et al. | |
| 2002/0106345 A1 | 8/2002 | Uhrich et al. | |
| 2002/0131998 A1 | 9/2002 | Martani | |
| 2002/0169212 A1 | 11/2002 | Stroble et al. | |
| 2002/0187187 A1 | 12/2002 | Ohki et al. | |
| 2003/0050305 A1 | 3/2003 | Tejada | |
| 2003/0055051 A1 | 3/2003 | Morizono et al. | |
| 2003/0109701 A1 | 6/2003 | Coppi et al. | |
| 2003/0119825 A1 | 6/2003 | Folger et al. | |
| 2003/0199482 A1 | 10/2003 | Seibert et al. | |
| 2003/0220306 A1 | 11/2003 | Simmons et al. | |
| 2003/0235589 A1 | 12/2003 | Demopulos et al. | |
| 2004/0001883 A1 | 1/2004 | Matsui et al. | |
| 2004/0015126 A1 | 1/2004 | Zierenberg et al. | |
| 2004/0024041 A1 | 2/2004 | Selzer | |
| 2004/0024042 A1 | 2/2004 | Breyer | |
| 2004/0037869 A1 | 2/2004 | Cleverly et al. | |
| 2004/0043992 A1 | 3/2004 | Tolba et al. | |
| 2004/0110747 A1 | 6/2004 | Altman | |
| 2004/0170687 A1 | 9/2004 | Hurd et al. | |
| 2004/0171611 A1 | 9/2004 | Trummlitz et al. | |
| 2004/0180092 A1 | 9/2004 | Henke et al. | |
| 2004/0198826 A1 | 10/2004 | Baiker et al. | |
| 2004/0204413 A1 | 10/2004 | Faour et al. | |
| 2004/0204472 A1 | 10/2004 | Briggs et al. | |
| 2004/0214753 A1 | 10/2004 | Britten et al. | |
| 2004/0229038 A1 | 11/2004 | Cooper et al. | |
| 2004/0234596 A1 | 11/2004 | Ohki et al. | |
| 2004/0253312 A1 | 12/2004 | Sowden et al. | |
| 2005/0038018 A1 | 2/2005 | Kanbe et al. | |
| 2005/0147664 A1 | 7/2005 | Liversidge et al. | |
| 2005/0187212 A1 | 8/2005 | Ohki et al. | |
| 2005/0187213 A1 | 8/2005 | Lang et al. | |
| 2005/0197332 A1 | 9/2005 | Altman | |
| 2005/0244491 A1 | 11/2005 | Ohki et al. | |
| 2005/0245510 A1 | 11/2005 | Friton et al. | |
| 2005/0277634 A1 | 12/2005 | Janott et al. | |
| 2005/0288280 A1 | 12/2005 | Friton et al. | |
| 2006/0079516 A1 | 4/2006 | Henke et al. | |
| 2006/0160793 A1 | 7/2006 | Altman | |
| 2006/0217431 A1 | 9/2006 | Daemmgen et al. | |
| 2007/0077296 A1 | 4/2007 | Folger et al. | |
| 2007/0099907 A1 | 5/2007 | Altman | |
| 2007/0193894 A1 | 8/2007 | Macken et al. | |
| 2007/0249727 A1 | 10/2007 | Martin et al. | |
| 2008/0064759 A1 | 3/2008 | Stamm et al. | |
| 2008/0132493 A1 | 6/2008 | Folger et al. | |
| 2008/0234380 A1 * | 9/2008 | Shapiro | A61K 31/195 514/565 |
| 2008/0280840 A1 | 11/2008 | Lang et al. | |
| 2010/0015184 A1 | 1/2010 | Tuel | |
| 2010/0233399 A1 | 9/2010 | Pradella et al. | |
| 2011/0083985 A1 | 4/2011 | Folger et al. | |
| 2011/0275618 A1 | 11/2011 | Folger et al. | |
| 2012/0077764 A1 * | 3/2012 | Freehauf | A61K 9/0019 514/30 |
| 2013/0178467 A1 | 7/2013 | Henke et al. | |
| 2014/0066440 A1 | 3/2014 | Folger et al. | |
| 2014/0113893 A1 | 4/2014 | Folger et al. | |
| 2014/0179639 A1 | 6/2014 | Lang et al. | |
| 2014/0332438 A1 | 11/2014 | Henke et al. | |
| 2015/0051198 A1 | 2/2015 | Folger et al. | |
| 2017/0035885 A1 | 2/2017 | Henke et al. | |

FOREIGN PATENT DOCUMENTS

| | | |
|---|---|---|
| CA | 1102802 | 6/1981 |
| CA | 2164100 A1 | 1/1995 |
| CA | 2166204 A1 | 1/1995 |
| CA | 2264626 A1 | 3/1998 |
| CA | 2326048 A1 | 10/1999 |
| CA | 2326517 A1 | 10/1999 |
| CA | 2404360 A1 | 9/2001 |
| CA | 2414063 A1 | 12/2001 |
| CA | 2469588 | 6/2003 |
| CA | 2503396 A1 | 5/2004 |
| CN | 1187356 A | 7/1998 |
| CN | 1546033 A | 11/2004 |
| DE | 3434707 A1 | 4/1985 |
| DE | 3700172 A1 | 7/1987 |
| DE | 4217971 C1 | 10/1993 |
| DE | 19729879 A1 | 1/1999 |
| DE | 10010123 A1 | 9/2001 |
| DE | 10024752 A1 | 11/2001 |
| DE | 10032132 A1 | 1/2002 |
| DE | 10300323 A1 | 10/2004 |
| EP | 0002482 A1 | 6/1979 |
| EP | 0034432 A2 | 8/1981 |
| EP | 0093999 A2 | 11/1983 |
| EP | 0127400 A2 | 12/1984 |
| EP | 0177870 A2 | 4/1986 |
| EP | 0179430 A2 | 4/1986 |
| EP | 0298192 A1 | 1/1989 |
| EP | 0306984 A1 | 3/1989 |
| EP | 0360246 A1 | 3/1990 |
| EP | 0390071 A1 | 10/1990 |
| EP | 0422681 A1 | 4/1991 |
| EP | 0465235 A1 | 1/1992 |
| EP | 0560329 A1 | 9/1993 |
| EP | 0629392 A1 | 12/1994 |
| EP | 0945134 A1 | 9/1999 |
| EP | 1082966 A1 | 3/2001 |
| EP | 1190714 A2 | 3/2002 |
| EP | 1568369 A1 | 8/2005 |
| ES | 2065846 A1 | 2/1995 |
| ES | 2159564 T3 | 10/2001 |
| FR | 2437838 A1 | 4/1980 |
| GB | 2087236 A | 5/1982 |
| GB | 2455875 A | 6/2009 |
| IT | 1251650 B | 5/1995 |
| JP | 47007352 Y1 | 3/1972 |
| JP | S52102416 A | 8/1977 |
| JP | S6191118 A | 5/1986 |
| JP | 1299230 A | 12/1989 |
| JP | H06157312 A | 6/1994 |
| JP | H0912426 A | 1/1997 |
| JP | 11139971 A | 5/1999 |
| JP | 2001170083 A | 6/2001 |
| JP | 2001172183 A | 6/2001 |
| JP | 2003535902 A | 12/2003 |
| JP | 3550782 B2 | 8/2004 |

(56) References Cited

FOREIGN PATENT DOCUMENTS

| | | | |
|---|---|---|---|
| JP | 2007197357 A | 8/2007 | |
| JP | 4018022 B2 | 12/2007 | |
| JP | 04321624 B2 | 8/2009 | |
| WO | 199301814 A1 | 2/1993 | |
| WO | 1994000420 A1 | 1/1994 | |
| WO | 1995009639 A1 | 4/1995 | |
| WO | 1995017178 A1 | 6/1995 | |
| WO | 1995018604 A1 | 7/1995 | |
| WO | 1996003387 A1 | 2/1996 | |
| WO | 1996003388 A1 | 2/1996 | |
| WO | 1996010999 A2 | 4/1996 | |
| WO | 1996011192 A1 | 4/1996 | |
| WO | 1996040102 A1 | 12/1996 | |
| WO | 1996040103 A1 | 12/1996 | |
| WO | 1996041625 A1 | 12/1996 | |
| WO | 1997003655 A1 | 2/1997 | |
| WO | 1997003667 A1 | 2/1997 | |
| WO | 1997017978 A1 | 5/1997 | |
| WO | 1997017989 A1 | 5/1997 | |
| WO | 1997029776 A1 | 8/1997 | |
| WO | 1997031631 A1 | 9/1997 | |
| WO | 1998009654 A1 | 3/1998 | |
| WO | 1998017250 A1 | 4/1998 | |
| WO | 1998031361 A1 | 7/1998 | |
| WO | 1998042318 A1 | 10/1998 | |
| WO | 199850045 A1 | 11/1998 | |
| WO | 1999009988 A1 | 3/1999 | |
| WO | 1999012524 A1 | 3/1999 | |
| WO | 1999027906 A1 | 6/1999 | |
| WO | 1999039730 A1 | 8/1999 | |
| WO | 1999049845 A1 | 10/1999 | |
| WO | 1999049867 A1 | 10/1999 | |
| WO | 1999055320 A1 | 11/1999 | |
| WO | 1999059634 A1 | 11/1999 | |
| WO | 1999062516 A1 | 12/1999 | |
| WO | 2000015195 A1 | 3/2000 | |
| WO | 2001006982 A2 | 2/2001 | |
| WO | 2001008689 A1 | 2/2001 | |
| WO | 2001037838 A1 | 5/2001 | |
| WO | 2001052897 A2 | 7/2001 | |
| WO | 2001064268 A1 | 9/2001 | |
| WO | 2001087343 A2 | 11/2001 | |
| WO | 2001097813 A2 | 12/2001 | |
| WO | 2002041899 A1 | 5/2002 | |
| WO | 2002085331 A1 | 10/2002 | |
| WO | 2002096216 A1 | 12/2002 | |
| WO | 2003049733 A1 | 6/2003 | |
| WO | 2003082297 A1 | 10/2003 | |
| WO | 2003097066 A1 | 11/2003 | |
| WO | 2004004776 A1 | 1/2004 | |
| WO | 2004026116 A2 | 4/2004 | |
| WO | 2004026313 A1 | 4/2004 | |
| WO | 2004037264 A1 | 5/2004 | |
| WO | 2004089379 A2 | 10/2004 | |
| WO | 2004103283 A2 | 12/2004 | |
| WO | 2005002542 A2 | 1/2005 | |
| WO | 2005004915 A2 | 1/2005 | |
| WO | 2005079806 A1 | 9/2005 | |
| WO | 2005097040 A1 | 10/2005 | |
| WO | 2005105101 | 11/2005 | |
| WO | 2005115386 A1 | 12/2005 | |
| WO | 2006000306 A1 | 1/2006 | |
| WO | 2006015942 A1 | 2/2006 | |
| WO | 2006061351 A1 | 6/2006 | |
| WO | 2006100213 A1 | 9/2006 | |
| WO | 2007039417 A1 | 4/2007 | |
| WO | 2007087214 A1 | 8/2007 | |
| WO | 2007135505 A2 | 11/2007 | |
| WO | 2008113149 A2 | 9/2008 | |
| WO | 2008152122 A2 | 12/2008 | |
| WO | 2009049304 A1 | 4/2009 | |
| WO | 2011046853 A1 | 4/2011 | |
| WO | 2011107150 A1 | 9/2011 | |
| WO | 2011107498 A1 | 9/2011 | |
| WO | 2011138197 A2 | 11/2011 | |

OTHER PUBLICATIONS

Tuerck et al., "Clinical Pharmacokinetics of Meloxicam". Arzneimittel-Forschung, vol. 47, No. 3, 1997, pp. 253-258.
Tunuguntla et al., "Management of Prostatitis". Prostate Cancer and Prostatic Diseases, vol. 5, No. 3, 2002, pp. 172-179.
Vippagunta et al., "Crystalline solids". Advanced Drug Delivery Reviews, vol. 48, 2001, pp. 3-26.
Wagenlehner et al., "Therapy of Prostatitis Syndrome". Der Urologe [A], vol. 40, No. 1, 2001, pp. 24-28. [English Abstract at p. 25].
Wan et al., "Incorporation and distribution of a low dose drug in granules". International Journal of Pharmaceutics, vol. 88, 1992, pp. 159-163.
Winfield, "Ophthalmic Products—Chelating agents". Pharmaceutical Practice, Churchill Livingstone, 2004, p. 268.
Yamashita et al., "Effects of Carprofen and Meloxicam with or without Butorphanol on the Minimum Alveolar concentration of Sevoflurane in Dogs". The Journal of Veterinary Medical Science, Jan. 2008, pp. 29-35. [Accessed at https://www.jstage.jst.go.jp/article/jvms/70/1/70_1_20/_pdf on Mar. 5, 2014].
Zaghawa et al., "Clinical and Etiological study on respiratory affections of sheep". Faculty of veterinary medicine—Sadat City—Menoufia University, Medicine and Infectious Diseases Department, Abstract, 10 pages. [Date Unknown].
Fitzpatrick et al., "Recognising and Controlling Pain and Inflammation in Mastitis". Proceedings of the British Mastitis Conference, Axient/Institute for Animal Health, Milk Development Council/Novartis Animal Health, 1998, pp. 36-44.
Gerritsen et al., "Prostaglandin Synthesis and Release from Cultured Human Trabecular-meshwork Cells and Scleral Fibroblasts". Experimental Eye Research, vol. 43, No. 6, 1986, pp. 1089-1102.
Giuliani et al., "Role of Antithrombotic Therapy in Cardiac Disease". Mayo Clinic Practice of Cardiology, Third Edition, Mosby, St. Louis, MO, 1996, pp. 1116-1121.
Gollackner et al., "Increased apoptosis of hepatocytes in vascular occulusion after orthotopic liver transplantation". Transplant International, vol. 13, No. 1, 2000, pp. 49-53.
Gowan, R., "Retrospective Analysis of Long-Term Use of Meloxicam in Aged Cats with Musculoskeletal Disorders and the Effect of Renal Function". Journal of Veterinary Internal Medicine, vol. 23, Abstract No. 87, 2009, p. 1347.
Gruet et al., "Bovine mastitis and intramammary drug delivery: review and perspectives". Advanced Drug Delivery Reviews, vol. 50, 2001, pp. 245-259.
Gunew et al., "Long-term safety, efficacy and palatability of oral meloxicam at 0.01-0.03 mg/kg for treatment of osteoarthritic pain in cats". Journal of Feline Medicine and Surgery, vol. 10, 2008, pp. 235-241.
Guth et al., "Pharmacokinetics and pharmacodynamics of terbogrel, a combined thromboxane A2 receptor and synthase inhibitor, in healthy subjects". British Journal of Clinical Pharmacology, vol. 58, No. 1, Jul. 2004, pp. 40-51.
Hansson et al., "Effect of local anaesthesia and/or analgesia on pain responses induced by piglet castration". Acta Veterinaria Scandinavica, vol. 53, No. 1, May 2011, pp. 1-9.
Hawkey et al., "Gastrointestinal Tolerability of Meloxicam Compared to Diclofenac in Osteoarthritis Patients". British Journal of Rheumatology, vol. 37, No. 9, 1998, pp. 937-945.
Herbort et al., "Anti-inflammatory Effect of Topical Diclofenac After Argon Laser Trabeculoplasty: Preliminary Results of a Placebo Controlled Study". Klin. Monatsbl. Augenheik, vol. 200, No. 5, May 1992, pp. 358-361.
Hirsch et al, "Investigation on the efficacy of meloxicam in sows with mastitis-metritis-agalactia syndrome". Journal of Veterinary Pharmacology and Therapeutics, vol. 26, 2003, pp. 355-360.
hittp://dictionary.reference.com/search?q=ambient, 2012.
Hydrated Silica Webpage; http://science.kosmix.com/topic/hydrated_silica; Kosmix Corporation, Apr. 21, 2011, pp. 1-14.
International Search Report and Written Opinion for PCT/EP2005/001549 dated Jun. 14, 2005.
Jain et al., "Antiplatelet therapy in acute coronary syndromes without persistent ST-segment elevation". Cardiovascular Drugs and Therapy, vol. 15, No. 5, Sep. 2001, pp. 423-436. [Abstract Only].

(56) References Cited

OTHER PUBLICATIONS

Kimura et al., "Effect of cilostazol on platelet agrregation and experimental thrombosis". Arzneimittel-Forschung, vol. 35, No. 7A, 1985, pp. 1144-1149. [Abstract Only].

Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.

Lane, David M., "Confidence Interval on the Mean". [Accessed at http://onlinestatbook.com/2/estimation/mean.html on Jun. 12, 2014], pp. 1-4.

Lascelles et al., "Nonsteroidal anti-inflammatory drugs in cats: a review". Veterinary Annesthesia and Analgesia, 2007, pp. 1-23.

Li et al., "Degradation mechanism and kinetic studies of a novel anticancer agent, AG2034". International Journal of Pharmaceutics, vol. 167, 1998, pp. 49-56.

Lieberman et al., "Tablet Formulation and Design" in Pharmaceutical Dosage Forms: Tablets, vol. 1, Second Edition, Marcel Dekker, Inc., New York, New York, 1989, pp. 105-108.

Little et al., "Importance of water for the health and productivity of the dairy cow". Research in Veterinary Science, vol. 37, No. 3, 1984, pp. 283-289, 1 page, Abstract Only. [Accessed at htt://www.ncbi.nlm.nih.gov/pubmed/6522821 on Feb. 8, 2016].

Luger et al., "Structure and physicochemical properties of meloxicam, a new NSAID". European Journal of Pharmaceutical Sciences, vol. 5, 1996, pp. 175-187.

Macdonald Campus of McGill University, "Mastitis in Dairy Cows", published online, Jul. 2003, pp. 1-12.

Masferrer et al., "Cyclooxygenase-2 Inhibitors: A New Approach to the Therapy of Ocular Inflammation". Survey of Ophthalmology, vol. 41, Supp. 2, Feb. 1997, pp. S35-S40.

McDonald et al., "Calpain inhibitor I reduces the activation of nuclear factor-KappaB and Organ Injury/Dysfunction in Hemorrhagic Shock". The FASEB Journal, vol. 15, Jan. 2001, pp. 171-186.

Medina, Joe, "Section XXIV—Principles of Compounding". Tech Lectures for the Pharmacy Technician, 2008, 12 pages.

Merriam Webster definition of Treatment accessed at [http://www.merriam-webster.com/dictionary/treatment on Dec. 19, 2013], 2 pages.

Mesh to Micron Conversion Chart, 2 pages. [Accessed at http://www.showmegold.org/news/mesh.htm on Aug. 22, 2013].

Nash et al., "A Relationship Between Screen Opening and Mesh Size for Standard Sieves"., Pharmaceutical Development and Technology, vol. 2, No. 2, 1997, pp. 185-186.

Nell et al., "Comparison of vedaprofen and meloxicam in dogs with muskuloskeletal pain and inflammation". Journal of Small Animal Practice, vol. 43, No. 5, May 2002, pp. 208-212 [Accessed at http://www.ncbi.nlm.nih.gov/pubmed/12038853 on Sep. 27, 2013]. Abstract Only, 1 page.

Noble et al., "Meloxicam". Drugs, vol. 51, No. 3, Mar. 1996, pp. 424-430.

Parikh et al., Binders and Solvents, Chapter 4, Handbook of Pharmaceutical Granulation Technology, First Edition, Marcel Dekker,1997, pp. 59-67.

Pharma Projects, Dialog File 928, Accession Nr. 0021312, Diclofenac, InSite Vision, 1996, 5 pages.

Pharmaceutical Excipient Encyclopedia, Yakuji Nippo Ltd., Tokyo, 1994, pp. 2-5.

Physicians' Desk Reference, 55th Edition, Medical Economics Company, Inc., 2001, pp. 981-984 and pp. 1404-1406.

Rantanen et al., "Process Analysis of Fluidized Bed Granulation". AAPS PharmsciTech, vol. 2, No. 4, Article 21, 2001, 8 pages.

Remington: The Science and Practice of Pharmacy, 19th Edition, vol. II, Mack Publishing Company, Easton, Pennsylvania, 1995, p. 1646.

RIRDC Equine Research News, "Equine Recurrent Uveitis (Moon Blindness) Research—Cause of Common Eye Problem Identified—". Jan. 2000, pp. 1-2. [Accessed at http://www.equusite.com/articles/health/healthUveitis.shtml on Feb. 8, 2016].

Robson et al., "Intrinsic acute renal failure (ARF) associated with non-steroidal anti-inflammatory drug (NSAId) use in juvenile cats undergoing routine desexing—16 cases 1998-2005". May 2006, Journal of Veterinary Internal Medicine, vol. 20, No. 3, Abst. 109, p. 740.

Rolfe et al., "The Physiological Significance of Mitochondrial Proton Leak in Animal Cells and Tissues." Bioscience Reports, vol. 17, No. 1, 1997, pp. 9-16.

Rudnic et al., "Oral Solid Dosage Forms"., Gennaro, Editior, Remington's Pharmaceutical Sciences, 18th Edition, Mack Publishing Company, Easton, PA, 1990, pp. 1633-1645 and pp. 1654-1655.

Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.

Schneeweis et al., "In Vivo and In Vitro Diclofenac Sodium Evaluation After Rectal Application of Soft Gelatine Capsules Enabling Application Induced Transformation (AIT) into a Seminsolid System of Liquid Crystals (SSLC) for Controlled Release". Pharmaceutical Research, vol. 14, No. 12, Dec. 1997, pp. 1726-1729.

Sciencelab.com, "Lactose, Monohydrate, Spray-Dried Powder, NF". Accessed at http://www.epoxy-paint.net/page/.S/PVAR/10419/SLL1453, Feb. 29, 2008, 2 pages.

Sharma et al., "Adsorption of Meloxican on Porous Calcium Silicate: Characterization and Tablet Formulation". AAPS PharmSciTech, vol. 6, No. 4, Article 76, 2005, pp. E618-E625.

Snyder et al., "Corticosteroid Treatment and Trabecular Meshwork Proteases in Cell and Organ Culture Supernatants". Experimental Eye Research, vol. 57, No. 4, 1993, pp. 461-468.

Sorbera et al., "Lumiracoxib Antiarthritic, COX-2 Inhibitor". Drugs of the Future, vol. 27, No. 8, Aug. 2002, pp. 740-747.

Stei et al., "Local Tissue Tolerability of Meloxicam, a New NSAID: Indications for Parental, Dermal and Mucosal Administration". British Journal of Rheumatology, vol. 35, Supp. 1, 1996, pp. 44-50.

"Committee for Veterinary Medicinal Products Meloxicam (Extension to bovine milk) Summary Report (4)". The European Agency for the Evaluation of Medicinal Products, Veterinary Medicines Evaluation Unit, Jul. 1999, pp. 1-2. [Accessed at http://www.ema.europa.eu/docs/en_GB/document_library/Maximum_Residue_limits_-_Report/2009/11/WC500014953.pdf].

"Committee for Veterinary Medicinal Products Meloxicam Summary Report (1)". The European Agency for the Evaluation of Medicinal Products, Jun. 1997, pp. 1-7.

"Committee for Veterinary Medicinal Products—Meloxicam (Extension to PIGS)—Summary Report (5)". The European Agency for the Evaluation of Medicinal Products, Veterinary Medicines and Information Technology, Dec. 2000, pp. 1-3.

"Determining Factors for Particle Size of a Table Formulation". Techceuticals Blog, Mar. 9, 2009, 2 pages. Accessed at [http://techceuticals.com/blog/?tag=particle-size on Oct. 1, 2015.].

"Edetic Acid and Edetates", Handbook of Pharmaceutical Excipients, American Pharmaceutical Association and the Pharmaceutical Society of Great Britain, 1986, pp. 108-110, 7 pages.

"Meloxicam Veterinary—Systemic"., The United States Pharmacopeial Convention, 2004, pp. 1-9. [Accessed at http://vetmed.tamu.edu/common/docs/public/aavpt/meloxicam.pdf on Aug. 16, 2013].

"Metacam (R) 0.5 mg/ml oral suspension for cats." Boehringer Ingelheim Datasheet, Web site: http://www.vetgb.com/vetgb_pdfs/rnetacamc_7a5c_vetgb.pdf> Accessed on Jun. 8, 2010.

"Metacam Professional Insert: Metacam® (meloxicam) 1.5 mg/mL Oral Suspension (equivalent to 0.05 mg per drop) Non-Steroidal anti-inflammatory drug for oral use in dogs only". Boehringer Ingelheim, Jan. 2005, 2 pages.

"Metacam(R)" FDA Animal & Veterinary Drug Labels, Web site: http://www.fda.gov/downloads/AnimalVeterinary/Products/ApprovedAnimalDrugProducts/DrugLabels/UCM050397.pdf> Accessed Jun. 8, 2010.

"METACAM—Community register of veterinary medicinal products" accessed online at http://pharmacos.eudra.org/F2/register/v004.htm, 2005.

"Staging System for Chronic Kidney Disease"., IRIS: International Renal Interest Society, 2006, pp. 1-4.

(56) References Cited

OTHER PUBLICATIONS

"Types of Solutions". University of Wisconsin, Stevens Point, Feb. 1, 2001, accessed at http://www.uwsp.edu/chemistry/tzamis/chem106pdfs/solutionexamples.pdf, Google date sheet included, 2 pages.
Abstract in English for IT1251650, 1995.
Abstract in English for JPH06157312, 1994.
Abstract in English of DE10024752, 2001.
Abstract in English of DE3434707, 1985.
Abstract in English of ES2065846, 1995.
Abstract in English of FR2437838, 1980.
Abstract in English of JP02906528, 1999.
Abstract in English of JP11139971, 1999.
Abstract in English of JP2001170083, 2001.
Abstract in English of JP2007197357, 2007.
Abstract in English of JP3550782, 2004.
Abstract in English of JP4018022, 2007.
Abstract in English of JP47007352, 1972.
Abstract in English of WO1999039730, 1999.
Altman et al., "Efficacy Assessment of Meloxicam, a Preferential Cyclooxygenase-2 Inhibitor, in Acute Coronary Syndromes Without ST-Segment Elevation: The Nonsteroidal Anti-Inflammatory Drugs in Unstable Angina Treatment-2 (NUT-2) Pilot Study". Circulation, vol. 106, 2002, pp. 191-195.
Ansel et al., "Dosage Form Design: Pharmaceutic and Formulation Considerations". Pharmaceutical Dosage Forms and Drug Delivery Systems, Seventh Edition, Lippincott Williams & Wilkins, Philadelphia, PA, 1999, pp. 66 and pp. 89.
Ansel et al., "Pharmaceutical Dosage Forms and Drug Delivery Systems". Seventh Edition, Lippincott Williams & Wilkins, Philadelphia, PA, 1999, pp. 77-87.
Bednarek et al., "Effect of steroidal and non-steroidal anti-imflammatory drugs in combination with long-acting oxytetracycline on non-specific immunity of calves suffering from enzootic bronchopneumonia". Veterinary Microbiology, vol. 96, 2003, pp. 53-67.
Bednarek et al., "The effect of steroidal and non-steroidal anti-inflammatory drugs on the cellular immunity of calves with experimentally-induced local lung inflammation". Veterinary Immunology and Immunopathology, vol. 71, 1999, pp. 1-15.
Bi et al., "Evaluation of Rapidly Disintegrating Tablets Prepared by a Direct Compression Method". Drug Development and Industrial Pharmacy, vol. 25, No. 5, 1999, pp. 571-581.
Boehringer Ingelheim; Metacam (Meloxicam) Now Approved for Pigs and Mastitis in Dairy Cows; May 2003 Press Release; pp. 1-2.
Budsberg et al., "Evaluation of intravenous administration of meloxicam for perioperative pain management rollowing stifle joint surgery in dogs". American Journal of Veterinary Research, vol. 63, No. 11, Nov. 2002, pp. 1557-1563.
Bunji, Kouho, "Tissue Damage Due to Infections" Drug Injection Handbook, Fundamentals of Blending Variation for Injection Drugs, Nanzando Co. Ltd., Tokyo, 1976, p. 5.
Chemical Abstracts, vol. 118, No. 18, Abstract No. 175803, Columbus, OHion, US May 1993 & JP-A-04 321 624 (Hisamitsu Pharm. Co.Inc., JP), Nov. 11, 1992, 1 page.
Cho et al., "In vitro effects of Actinobacillus pleuropneumoniae on inducible nitric oxide synthase and cyclooxygenase-2 in porcine alveolar macrophages". American Journal of Veterinary Research, vol. 64, No. 12, Dec. 2003, pp. 1514-1518.
Clarke et al., "Feline osteoarthritis: a prospective study of 28 cases". Journal of Small Animal Practice, vol. 47, 2006, pp. 439-445.
D'Yakov et al., "Long term use of Tamsulosin (omnic®) in Patients with Chronic Prostatitis". Urologiia, vol. 5, 2002, pp. 10-12.
Del Tacca et al., "Efficacy and Tolerability of Meloxicam, a COX-2 Preferential Nonsteroidal Anti-Inflammatory Drug". Clinical Drug Investigation, vol. 22, No. 12, 2002, pp. 799-818.
Dellabella et al., "Conservative Managment of Juxtavesical Calculi with Tamsulosin". European Urology Supplements, vol. 2, No. 1, 2003, p. 81.
Dow Chemicals Brochure, entitled "Using METHOCEL cellulose ethers for controlled release of drugs in hyrophilic matrix systems." Publication Jul. 2000, Form No. 198-02075-700 AMS, pp. 1-36.
Dunn et al., "Tamsulosin: A Review of its Pharmacology and Therapeutic Efficacy in the Management of Lower Urinary Tract Symptoms". Drugs & Aging, vol. 19, No. 2, 2002, pp. 132-161.
Engelhardt et al., "Meloxicam: Influence on Arachidonic Acid Metabolism". Biochemical Pharmacology, vol. 51, 1996, pp. 21-28.
Ettmayer et al., "Lessons Learned from Marketed and Investigational Prodrugs". Journal of Medicinal Chemistry, vol. 47, No. 10, May 2004, pp. 2393-2404.
European Search Report for EP10155400 dated Jun. 9, 2010.
European Search Report for EP10162015 dated Aug. 30, 2010.
Farkouh et al., "Comparison of lumiracoxib with naproxen and ibuprofen in the Therapeutic Arthritis Research and Gastrointestinal Event Trial (TARGET), cardiovascular outcomes: randomised controlled trial". Lancet, vol. 364, Aug. 2004, pp. 675-684.
Fiedorczyk, D.M., "Renial Failure in Cats". Misericordia University, Internet Archive Date: Sep. 7, 2006, http://www.misericordia.edu/honorus/dfpaper.cfm [Retrieved on Dec. 12, 2012].
Fitzgerald et al., "COX-2 inhibitors and the cardiovascular system". Clinical and Experimental Rheumatology, vol. 19, No. 6, Supp. 25, Nov. 2001, pp. S31-S36.

\* cited by examiner

MELOXICAM FOR THE TREATMENT OF RESPIRATORY DISEASES IN PIGS

BACKGROUND OF THE INVENTION

1. Technical Field

The invention relates to the use of meloxicam or a pharmaceutically acceptable salt thereof for preparing a pharmaceutical composition for the treatment or prevention of respiratory diseases in pigs.

2. Background Information

Respiratory disease in pigs belongs to the most important health problems in swine production. Porcine respiratory disease is primarily caused by infectious agents, but environmental factors have a strong influence. The relevant pathogens include mycoplasmas, bacteria, and viruses (e.g., G. Christensen, V. Sorensen, and J. Mousing, *Diseases of the Respiratory System*, In: *Diseases of Swine*, B. E. Straw, S. D'Allaire, W. L. Mengeling, & D. J. Taylor (eds), Iowa State University Press, Ames, Iowa (1999) pp. 913-940).

The most important measures for the control of porcine respiratory disease are to improve herd management and housing conditions and introduce a vaccination program. However, if pigs have developed respiratory disease, they have to be treated.

Current therapy of porcine respiratory disease includes treatment with antibiotics. The successful use of various types of antibiotics is described, including β-lactams, quinolones, and tetracyclines (e.g., I. Lang, M. Rose, E. Thomas, & E. Zschiesche, *A Field Study of Cefquinome for the Treatment of Pigs with Respiratory Disease*, Revue Med Vet 8-9, (2002) pp. 575-580).

It is known that cyclooxygenase-2 (COX-2) plays a relevant role in the pathophysiology of porcine pleuropneumonia caused by *Actinobacillus pleuropneumoniae*. Isolated porcine alveolar macrophages increase their COX-2 activity after exposure to *Actinobacillus pleuropneumoniae* (W. S. Cho & C. Chae, In vitro *Effects of Actinobacillus pleuropneumoniae on Inducible Nitric Oxide Synthase and Cyclooxygenase-2 in Porcine Alveolar Macrophages*, Am J Vet Res 64, (2003) pp. 1514-1518). Moreover, in situ hybridization (W. S. Cho & C. Chae, *Expression of Cyclooxygenase-2 in Swine Naturally Infected with Actinobacillus pleuropneumoniae*, Vet Pathol 40, (2003) pp. 25-31) and immunohistochemistry (W. S. Cho & C. Chae, *Immunohistochemical Detection of Cyclooxygenase-2 in Lungs of Pigs Naturally Infected with Actinobacillus pleuropneumoniae*, J Comp Pathol 127, (2002) pp. 274-279) showed increased COX-2 expression in lungs of pigs naturally infected with *Actinobacillus pleuropneumoniae*.

Moreover, it is well-known that acetylsalicylic acid (aspirin) can be used for the treatment of pigs with respiratory disease. However, little information on controlled clinical studies is available: for a review, see A. Laval, *Utilisation des Anti-inflammatoires chez le Porc*, Rec Méd Vét 168 (8/9) (1992) pp. 733-744. Ketoprofen, and, to a lesser extent, flunixin decrease fever induced by experimental infection with *Actinobacillus pleuropneumoniae* (J. M. Swinkels, A. Pijpers, J. C. Vernooy, A. Van Nes, & J. H. Verheijden, *Effects of Ketoprofen and Flunixin in Pigs Experimentally Infected with Actinobacillus pleuropneumoniae*, J Vet Pharmacol Ther 17, (1994) pp. 299-303). However, no effects on lung lesions were observed. Ketoprofen was further tested in a controlled, blinded clinical field study (M. F. De Jong, O. Sampimon, J. P. Arnaud, G. Theunissen, G. Groenland, & P. J. Werf, *A Clinical Study with a Non Steroid Antiinflammatory Drug*, 14, (1996) 659 IPVS). In this study, ketoprofen had no effect on clinical score, relapse, or cure rate.

Indomethacin alleviated experimental endotoxin-induced respiratory failure in pigs (N. C. Olson, T. T. Brown, J. R. Anderson, & D. L. Anderson, *Dexamethasone and Indomethacin Modify Endotoxin-Induced Respiratory Failure in Pigs*, J Appl Physiol 58, (1985) pp. 274-284).

Meloxicam is a non-steroidal anti-inflammatory compound that belongs to the oxicam class and exerts potent anti-inflammatory, anti-exudative, and anti-pyretic activity. The efficacy of meloxicam as an adjunctive therapy in the treatment of respiratory infections in cattle has been widely proven. Recently meloxicam was approved for the treatment of MMA (A. Hirsch et al., J Vet Pharmacol Therap 26 (2003) pp. 355-360) and locomotor disorders in pigs (G. Friton et al., Berl Münch Tierärztl Wschr 116 (2003) pp. 421-426).

A review article (P. Lees, *The Pharmacokinetics of Drugs Used in the Treatment of Respiratory Diseases in Cattle and Pigs*, (1991) pp. 67-74, Hatfield, U.K. Proc. Royal Vet. Coll.) focuses on pharmacokinetics used in the treatment of respiratory disease in cattle and pigs; however, non-steroidal anti-inflammatory drugs data for pigs was almost entirely lacking and only lists data for cattle including meloxicam.

The use of meloxicam in conjunction with antibiotics in bovine respiratory disease is well-established (H. Schmidt, H. Philipp, E. Salomon, & K. Okkinga, *Effekte der zusäitzlichen Gabe von Metacam (Meloxicam) auf den Krankheitsverlauf bei Rindern mit Atemwegserkrankungen*, Der praktische Tierarzt 81 (2000) pp. 240-244) and registered in the EU. However, to date no information on the use of meloxicam in pigs with respiratory disease is publicly available.

Since the pharmacokinetics in pigs and cattle differ substantially for meloxicam (plasma half-time in cattle is 26 hours whereas it is 2.5 hours in pigs), there is no expectation that the successful use of meloxicam in cattle should also be beneficial for pigs. Moreover, the causative agents for bovine and porcine respiratory disease differ substantially.

The problem underlying the present invention was to provide a medication for the prevention or treatment of respiratory diseases in pigs, one of the most important health problems in swine production.

BRIEF DESCRIPTION OF THE INVENTION

It has been found surprisingly that meloxicam can be used for the treatment or prevention of respiratory diseases in pigs.

Accordingly, the invention relates to the use of meloxicam or a pharmaceutically acceptable salt thereof for preparing a pharmaceutical composition for the treatment or prevention of respiratory diseases in pigs.

Moreover, the invention relates to a method of treating or preventing respiratory diseases in pigs, which method comprises administering an effective amount of meloxicam to the pigs in need thereof.

Furthermore, the invention relates to veterinary preparation containing meloxicam as well as at least one antibiotic selected from the group consisting of β-lactams, quinolones, tetracyclines, sulfonamides, fenicoles, and macrolides.

Another aspect of the invention is a ready-to-use two-component system for the treatment of respiratory diseases in pigs, wherein:

(a) one component contains meloxicam and a pharmaceutically acceptable carrier; and (b) the other component contains at least one antibiotic selected from the group consisting of β-lactams, quinolones, tetracyclines, sulfonamides, fenicoles, and macrolides and a pharmaceutically acceptable carrier.

Still another aspect of the invention is an article of manufacture comprising packaging material contained within which is a composition consisting of meloxicam and a pharmaceutically acceptable carrier, and a label which indicates that the composition can be used to treat or prevent respiratory diseases in pigs.

DETAILED DESCRIPTION OF THE INVENTION

Figure 1:
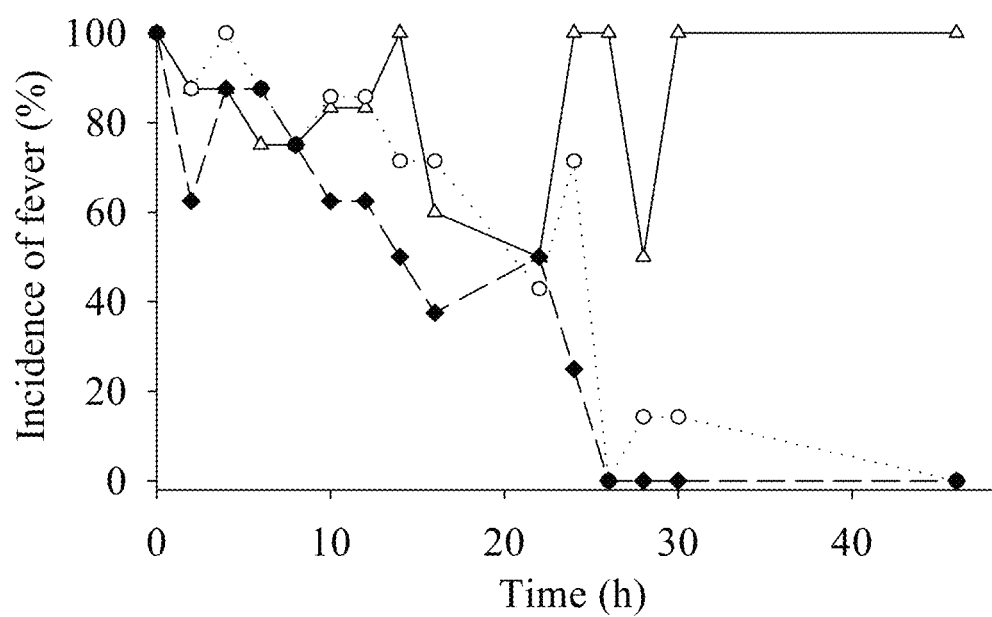
FIG. 1 shows the incidence of fever (rectal temperature ≥40.56° C.) in percent following the first treatment in a group of pigs treated with oxytetracycline and meloxicam (♦), in a group of pigs treated with oxytetracycline alone (o), and in the untreated control (Δ).

Preferably the invention relates to the use of meloxicam or a pharmaceutically acceptable salt thereof for preparing a pharmaceutical composition in a form suitable for systemic or oral administration for the treatment or prevention of respiratory diseases in pigs. Meloxicam (4-hydroxy-2-methyl-N-(5-methyl-2-thiazolyl)-2H-1,2-benzothiazine-3-carboxamide-1,1-dioxide) of formula

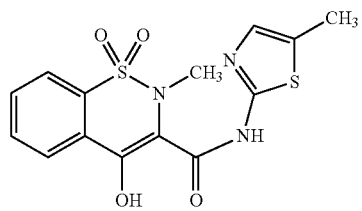 [SMILES: Cc1cnc(NC(=O)C2=C(O)c3ccccc3S(=O)(=O)N2C)s1]

is an active substance which belongs to the group of NSAIDs (non-steroidal-anti-inflammatory drugs). Meloxicam and the sodium and meglumine salt thereof (N-methyl-D-glucamine salt) are described in EP-A-0 002 482 (corresponding to U.S. Pat. No. 4,233,299), each of which is hereby incorporated by reference.

Meloxicam may be used according to the invention in the form of a physiologically acceptable acid addition salt. By physiologically acceptable acid addition salts are meant, according to the invention, the meglumine, sodium, potassium, or ammonium salt, preferably the meloxicam meglumine salt.

In a further preferred embodiment, the pharmaceutical composition is administered corresponding to a daily dose of meloxicam ranging from 0.01 mg/kg to 5.0 mg/kg, preferably from 0.1 mg/kg to 3.5 mg/kg, in particular from 0.2 mg/kg to 2.0 mg/kg.

The pharmaceutical composition is preferably administered in a form suitable for injection, in particular for intramuscular injection, or in form of water soluble granules for administration via drinking water or as top dressing on feed.

A suitable injection formulation is disclosed, for example, in Example 25 of EP-A-0 002 482. Furthermore, such injection solutions may additionally contain excipients selected from among citric acid, lecithin, gluconic acid, tartaric acid, phosphoric acid and EDTA or the salts thereof as disclosed in the Examples 1 to 5 of the International Patent Application WO 01/97813 (corresponding to U.S. Patent App. Pub No. 2002/0035107), each of which is hereby incorporated by reference. Moreover, an injection solution of meloxicam for needleless injections is disclosed in the International Patent Application WO 03/049733 (corresponding to U.S. Patent App. Pub No. 2003/0119825), each of which is hereby incorporated by reference.

Suitable water soluble granules for administration via drinking water or as top dressing on feed are, for example, disclosed in the International Patent Application PCT/EP03/11802 (corresponding to U.S. Patent App. Pub No. 2004/0234596), each of which is hereby incorporated by reference.

In a preferred embodiment of the invention, the meloxicam granules contain a binder which may be selected from among hydroxypropylmethylcellulose, polyvinylpyrrolidone, gelatine, starch, and polyethylene glycol ether, preferably hydroxypropylmethylcellulose, polyvinylpyrrolidone, and polyethylene glycol ether, and most preferably hydroxypropylmethylcellulose and polyvinylpyrrolidone.

In another preferred embodiment of the invention, meloxicam granules contain a sweetener, which may be selected from among sodium saccharine, aspartame, and SUNETT® (acesulfame K), preferably sodium saccharine or aspartame.

Particularly preferred according to the invention are meloxicam granules containing a flavoring agent which may be selected from among vanilla, honey flavoring, apple flavoring, and contramarum, preferably honey flavoring and apple flavoring.

Also particularly preferred are meloxicam granules in which the carrier is selected from among lactose, glucose, mannitol, xylitol, sucrose, and sorbitol, preferably glucose, lactose, or sorbitol, more preferably glucose or lactose, and most preferably glucose.

Most preferred are the following granules of meloxicam recipes:

Example A: 0.6% Meloxicam Granules

|  | g/100 g |
| --- | --- |
| Meloxicam | 0.6 |
| Meglumine | 0.42 |
| Hydroxypropylmethylcellulose | 3.00 |
| Povidone | 2.00 |
| Glucose monohydrate | 93.98 |

Example B: 1.2% Meloxicam Granules

|  | g/100 g |
| --- | --- |
| Meloxicam | 1.2 |
| Meglumine | 0.84 |
| Hydroxypropylmethylcellulose | 3.00 |
| Collidone 25 | 2.0 |
| Glucose Monohydrate | 92.96 |

Example C: 0.6% Meloxicam Granules

|  | g/100 g |
| --- | --- |
| Meloxicam | 0.6 |
| Meglumine | 0.42 |
| Pharmacoat 606 | 4.0 |
| Macrogol 6000 | 1.0 |
| Acesulfame K | 0.3 |
| Lactose | 93.68 |

Example D: 0.6% Meloxicam Granules

|  | g/100 g |
| --- | --- |
| Meloxicam | 0.6 |
| Meglumine | 0.42 |
| Pharmacoat 606 | 4.75 |
| Macrogol 6000 | 0.25 |
| Acesulfame K | 0.3 |
| Liquid vanilla flavoring | 0.05 |
| Lactose | 93.63 |

Particularly preferred are meloxicam granules in which the content of meloxicam is between 0.05% and 4%, preferably between 0.1% and 2%, preferably between 0.3% and 1.8%, more preferably between 0.4% and 1.5%, and most preferably 1.2%. Also particularly preferred are meloxicam granules which contain meglumine and meloxicam in a molar ratio of about 9:8 to 12:8, preferably 10:8.

Meloxicam can be used according to the invention to treat or prevent respiratory diseases in any breed of swines. Preferably pigs selected from the swine breeds American Landrace, American Yorkshire, Angeln Saddleback, Arapawa Island, Ba Xuyen, Bantu, Bazna, Beijing Black, Belarus Black Pied, Belgian Landrace, Bentheim Black Pied, Berkshire, Black Slavonian, British Landrace, British Lop, Bulgarian White, Cantonese, Chester White, Czech Improved White, Danish Landrace, Dermantsi Pied, Duroc, Dutch Landrace, Fengjing, Finnish Landrace, French Landrace, German Landrace, Gloucestershire Old Spots, Guinea Hog, Hampshire, Hereford, Hezuo, Iberian, Italian Landrace, Jinhua, Kele, Krskopolje, Kunekune, Lacombe, Large Black, Large Black-white, Large White, Lithuanian Native, Mangalitsa, Meishan, Middle White, Minzhu, Mong Cai, Mukota, Mora Romagnola, Moura, Mulefoot, Neijiang, Ningxiang, Norwegian Landrace, Ossabaw Island, Oxford Sandy and Black, Philippine Native, Pietrain, Poland China, Red Wattle, Saddleback, Spots, Swabian-Hall, Swedish Landrace, Tamworth, Thuoc Nhieu, Tibetan, Turopolje, Vietnamese Potbelly, Welsh, and Wuzhishan, in particular American Landrace, Belgian Landrace, British Landrace, Danish Landrace, Dutch Landrace Finnish Landrace, French Landrace, German Landrace, Italian Landrace, and Pietrain can be treated with meloxicam according to the present invention.

Furthermore preferred is the administration of meloxicam is in conjunction with an antibiotic, preferably selected from the group consisting of β-lactams, quinolones, tetracyclines, sulfonamides, fenicoles, and macrolides. Most preferred are amoxicillin, oxytetracycline, florfenicol, tylosin, tilmicosin, and sulfamethazine.

The dose of antibiotic is not critical per se and depends strongly on the different efficacies of the antibiotics used. As a rule up to 150.0 mg/kg, preferably from 0.1 mg/kg to 120 mg/kg, in particular from 10 mg/kg to 110 mg/kg of an antibiotic are co-administered together with meloxicam.

The following dose ranges are most preferred:
Amoxicillin: 5 mg/kg to 30 mg/kg, in particular about 10 mg/kg;
Oxytetracycline: 20 mg/kg to 70 mg/kg, in particular about 30 mg/kg;
Florfenicol: 10 mg/kg to 20 mg/kg, in particular about 15 mg/kg;
Tylosin: 10 mg/kg to 25 mg/kg, in particular about 16 mg/kg;
Tilmicosin: 5 mg/kg to 30 mg/kg, in particular 10 mg/kg to 20 mg/kg; and
Sulfamethazine: 80 mg/kg to 150 mg/kg, in particular about 100 mg/kg.

The phrase "co-administration" (or "administration in conjunction with"), in defining use of meloxicam and an antibiotic, is intended to embrace administration of each agent in a sequential manner in a regimen that will provide beneficial effects, in particular, reduction of the symptoms of the respiratory disease in the affected pig of the drug combination. The phrase also is intended to embrace co-administration of these agents in a substantially simultaneous manner, such as in a single capsule or injection solution having a fixed ratio of these active agents or in multiple, separate capsules for each agent.

Accordingly, meloxicam and the antibiotic may be co-administered in a combined form, or separately or separately and sequentially wherein the sequential administration is preferably close in time.

Preferably the medicament according to this invention is used for the prevention or treatment of Porcine Respiratory Disease Complex in growing or fattening pigs; or for the prevention or treatment of respiratory diseases in pigs caused by mycoplasmas, in particular *Mycoplasma hyopneumoniae, Mycoplasma hyorhinis*, for the prevention or treatment of respiratory diseases in pigs caused by bacteria in particular *Actinobacillus* spp., in particular *Actinobacillus pleuropneumoniae, Bordetella bronchiseptica, Pasteurella multocida, Arcanobacterium pyogenes, Streptococcus* spp., and *Staphylococcus* spp., or for the prevention or treatment of respiratory diseases in pigs caused by viruses, in particular Swine Influenza Virus, Aujetzky's Virus, Porcine Reproductive and Respiratory Syndrome Virus, Porcine Circovirus, and Transmissible Gastroenteritis and Porcine Respiratory Coronavirus.

Most preferably the medicament according to this invention is used for the prevention or treatment of respiratory diseases in pigs caused by *Mycoplasma hyopneumoniae, Actinobacillus pleuropneumoniae, Bordetella bronchiseptica, Pasteurella multocida, Streptococcus suis*, Swine Influenza Virus, and Porcine Reproductive and Respiratory Syndrome Virus.

The Examples that follow serve to illustrate the use of meloxicam according to the invention. They are intended solely as possible procedures described by way of example, without restricting the invention to their content.

Example 1: Efficacy of Meloxicam in Pigs with Experimental *Actinobacillus Pleuropneumoniae* Infection The study was a controlled, randomized, and blinded exploratory study under experimental conditions with a parallel group design.

Crossbred pigs of about 10 weeks of age were challenged with a single intranasal inoculation of *Actinobacillus pleuropneumoniae*. The next day, pigs were included in the study and treated if they fulfilled the following inclusion criteria: rectal temperature ≥40° C. and clinical symptoms of acute or subacute infectious respiratory disease.

Twenty-four (12 castrated male and 12 female) pigs were included and randomly allocated to three treatment groups with 8 pigs per group. The treatment groups were:

| Group | Treatment |
|---|---|
| 1 | untreated |
| 2 | oxytetracycline |
| 3 | oxytetracycline and meloxicam |

Meloxicam was administered as 0.5% solution, at 0.5 mg/kg daily on three consecutive days, oxytetracycline as 20% long-acting solution (OXYTET® 200) at 20 mg/kg as single injection.

Relevant criteria for the evaluation of efficacy were incidence of fever, clinical parameters of respiratory disease, deaths, and lung lesions at necropsy 10 days after first treatment or after spontaneous death. The percentage of affected lung tissue was calculated by lobe and averaged for the total lung.

Challenge with *Actinobacillus pleuropneumoniae* lead to severe pleuropneumonia within 12 hours.

The incidence of fever (rectal temperature ≥40.56° C.) following the first treatment was lower in group 3 (♦) than in groups 1 (Δ), and 2 (o) (cp. FIG. 1).

The best treatment response in clinical parameters was observed in group 3.

The number of pigs which died during the three days following first treatment is displayed below.

| Group (n = 8 per group) | Deaths |
|---|---|
| 1 | 7 |
| 2 | 1 |
| 3 | 0 |

The mean extent of lung lesions was less severe in group 3 than in the other groups (see below).

| Group | Lung lesions (%) |
|---|---|
| 1 | 60 |
| 2 | 35 |
| 3 | 14 |

Meloxicam in addition to antibiotic treatment effectively reduced fever, clinical symptoms of respiratory disease, deaths, and the extent of lung lesions in pigs with experimental *Actinobacillus pleuropneumoniae*-infection.

Example 2: Efficacy of Meloxicam in Drinking Water in Experimental Swine Influenza Virus Infection The aim of this study was to test the efficacy of meloxicam granules dissolved in drinking water in pigs experimentally infected with Swine Influenza Virus (SIV).

The study was an open, negative controlled randomized laboratory study carried out according to GCP at one site.

Meloxicam granules containing 6 mg meloxicam per gram were offered to the pigs in the treatment groups (A+B) via drinking water in a concentration of 1 g granules per liter drinking water ad libitum for 7 consecutive days. This resulted in an actual meloxicam uptake of 0.8 mg per kg body weight per day. The pigs in the control group (C) received municipal drinking water ad libitum.

30 pigs were infected with SIV on study day 0. 10 pigs were allocated to each of the three groups A, B, and C. Treatment (groups A and B) started after SIV challenge on the same day.

The study animals were clinically examined daily on study days 0 to 7 and 14. They were weighed on study days 7 and 14. All animals of group A and 5 animals of group C were euthanized and necropsied on study day 7; the remaining study animals, group B and 5 study animals of group C, on study day 14.

Figure 2:
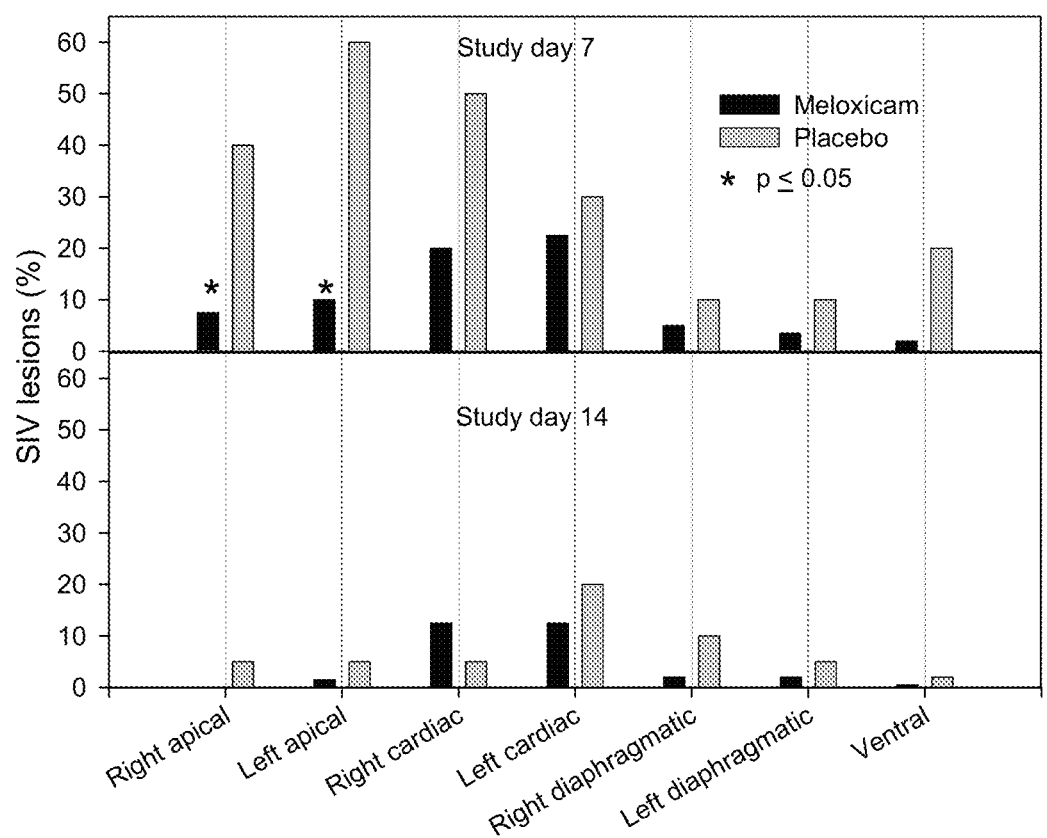
FIG. 2 shows the efficacy of meloxicam in drinking water in reducing lung lesions caused by experimental Swine Influenza Virus (SIV) infection on study days 7 and 14.

It is the major finding of this study that meloxicam granules administered continuously in the drinking water at an approximate daily dose of 0.8 mg/kg body weight significantly alleviated the development of lung lesions caused by experimental infection with SIV during the first week after challenge. FIG. 2 shows the quantity of lung lesions by lung lobe on study days 7 and 14.

On study day 7 the percentage of lung tissue affected with SIV-related lesions (median value) was 8.9% in meloxicam group A and 23.8% in the control group (5 study animals of group C).

Moreover, meloxicam-treated pigs reached significantly higher weight gains during the two weeks following infection than untreated controls. Mean daily weight gain in the interval study day 0 to 7 was 557 g in meloxicam group A and 257 g in the control (5 study animals of group C). In the interval study day 0 to 14, mean daily weight gain was 629 g in meloxicam group B and 486 g in the control (5 study animals of group C).

The area under the curve of the clinical index score (CIS), a sum of the relevant clinical parameters, over study days 0 to 7 was significantly smaller in groups A and B than in group C.

Thus oral treatment with meloxicam granules at a dose of 0.8 mg meloxicam per kg body weight per day for 7 consecutive was an efficacious treatment for SIV infection.

Example 3: Field Trial Regarding the Effect of Meloxicam in the Porcine Respiratory Disease Complex (PRDC) in Growing/Fattening Pigs Materials and Methods A medium scale farm (560 sows) with a previous history of recurring PRDC episodes was selected. A double-blinded randomized study was carried out with the selection of 162 growing animals with a mean age of 90 days at the onset of PRDC clinical signs. Animals were randomly allocated to 8 pens and divided into two treatment groups, with respect to equal sex ratio, same housing and feeding conditions and genetic background. Group 1 (PC) received 800 ppm chlorotetracycline in the feed over 8 consecutive days plus a single IM injection of a placebo (isotonic saline) at d0 (start of the trial, n=82). Group 2 (M) received 800 ppm chlorotetracycline in the feed over 8 consecutive days plus a single IM injection of 0.4 mg/kg bodyweight meloxicam (METACAM® 2%, Boehringer Ingelheim GmbH) at d0 (n=80). Clinical parameters were assessed as the daily Respiratory Score (RS), using a 3 point score (0=absence of signs to 3=abdominal breathing and disordered general condition) over 8 consecutive days and the total number of additional required injectable medications (AIM). Growth performance data for each group included the Average Daily Gain (ADG) for the following trial periods: d90 to d117, d117 to d170 (slaughtering), and d90 to d170 of age. Mortality was also calculated for these time periods. Slaughterhouse records per group, included the percentage of each lung surface (LS) affected by chronic and acute respiratory lesions.

Student's t-Test and Pearson's Chi-Square Test were used for the consequent comparisons of means and frequencies between trial groups.

Results and Discussion

RS and AIM in the meloxicam group were significantly lower (p<0.05) compared to the control group. Same applies for LS affected by acute lesions (p<0.01), while no differences were observed for LS in chronic cases (Table 1).

TABLE 1

RS, LS: Mean (SD); AIM number (%)

| | Treatment Group | | |
|---|---|---|---|
| | PC | M | Significance |
| RS | 0.70 (0.63)$^a$ | 0.50 (0.51)$^b$ | p = 0.0289 |
| AIM (%) | 10/82 (12.2%)$^a$ | 2/80 (2.5%)$^b$ | $x^2$ = 4.226 |
| LS(chronic) | 5.96 (2.28)$^a$ | 5.91 (2.32)$^a$ | p = 0.893 |
| LS (acute) | 3.71 (1.81)$^a$ | 2.64 (2.03)$^b$ | p = 0.0007 |

$^{a,b}$Values in a row with different superscripts differ significantly

The analysis of growth performance data revealed significant differences between groups at d90 to d117 (p<0.05, Table 2).

TABLE 2

ADG: Mean (SD)

| | Trial Period | | |
|---|---|---|---|
| Group | d90 to d117 | d117 to d170 | d90 to d170 |
| PC | 0.64 (0.09)$^a$ | 0.89 (0.06)$^a$ | 0.81 (0.03)$^a$ |
| M | 0.67 (0.10)$^b$ | 0.89 (0.06)$^a$ | 0.82 (0.03)$^a$ |

$^{a,b}$Values in a column with different superscripts differ significantly (p < 0.05)

TABLE 3

Mortality: Number of animals/group (%)

| | Trial Period | | |
|---|---|---|---|
| Group | d90 to d117 | d117 to d170 | d90 to d170 |
| PC | 6/82 (7.32%)$^a$ | 1/76 (1.22%) | 7/82 (8.54%) |
| M | 0/80 (0.00%)$^b$ | 1/80 (1.25%) | 1/80 (1.25%) |

$^{a,b}$Values in a column with different superscripts differ significantly (p < 0.05)

Under the conditions of this study, the reduction of the prevalence of respiratory signs as well as the reduced overall number of required injectable antibiotic medications are indicative for the potent anti-inflammatory activity of meloxicam. The latter could become a valuable adjunctive measure, especially when respiratory distress is associated with remarkable reduction of the feed intake. The initial differences in growth performance and in mortality rate could be explained by the fact that meloxicam, when combined with proper antimicrobial medication, contributes to faster recovery from a respiratory inflammation and faster restoring of the distorted growth rate of affected animals. Further research on the evaluation of feed intake and the use of meloxicam in PRDC recurring episodes is required.

What is claimed:

1. A method of treating or preventing a respiratory disease caused by a virus in a pig, the method comprising administering to a pig suffering from a respiratory disease an effective amount of meloxicam or a pharmaceutically acceptable salt thereof, wherein the disease is caused by Swine Influenza Virus, Aujetzky's Virus, Porcine Reproductive and Respiratory Syndrome Virus, Porcine Circovirus, or Transmissible Gastroenteritis and Porcine Respiratory Coronavirus wherein meloxicam or a pharmaceutically acceptable salt thereof is administered in the form of granules and wherein the granules further comprise:
   meglumine;
   a carrier selected from the group consisting of lactose, glucose, mannitol, xylitol, sucrose, and sorbitol; and a binder selected from the group consisting of hydroxypropylmethylcellulose, polyvinylpyrrolidone, gelatine, starch, and polyethylene glycol ether.

2. The method of claim 1, wherein the disease is Porcine Respiratory Disease Complex and the pig is a growing or fattening pig.

3. The method of claim 1, wherein the meloxicam or a pharmaceutically acceptable salt thereof is administered systemically or orally.

4. A method of treating or preventing a respiratory disease caused by a virus in a pig, the method comprising administering to a pig suffering from a respiratory disease an effective amount of meloxicam or a pharmaceutically acceptable salt thereof, wherein the disease is caused by Swine Influenza Virus, Aujetzky's Virus, Porcine Reproductive and Respiratory Syndrome Virus, Porcine Circovirus, or Transmissible Gastroenteritis and Porcine Respiratory Coronavirus, and the meloxicam or a pharmaceutically acceptable salt thereof is administered by injection wherein meloxicam or a pharmaceutically acceptable salt thereof is administered in the form of granules and wherein the granules further comprise:
   meglumine;
   a carrier selected from the group consisting of lactose, glucose, mannitol, xylitol, sucrose, and sorbitol; and a binder selected from the group consisting of hydroxypropylmethylcellulose, polyvinylpyrrolidone, gelatine, starch, and polyethylene glycol ether.

5. The method of claim 1, wherein the meloxicam or a pharmaceutically acceptable salt thereof is administered in a daily dose ranging from 0.01 mg/kg to 5.0 mg/kg.

6. The method of claim 1, wherein the meloxicam or a pharmaceutically acceptable salt thereof is administered via drinking water or as top dressing on feed in soluble granules.

7. The method of claim 1, further comprising:
   administering an antibiotic to the pig, wherein the antibiotic is selected from the group consisting of β-lactams, quinolones, tetracyclines, sulfonamides, fenicoles, macrolides, and any one or more combinations thereof.

8. The method of claim 7, wherein the antibiotic is oxytetracycline or chlorotetracycline.

9. The method of claim 7, wherein the antibiotic is administered in conjunction with the meloxicam or a pharmaceutically acceptable salt thereof.

* * * * *